(12) United States Patent
Brannan

(10) Patent No.: US 9,943,367 B2
(45) Date of Patent: *Apr. 17, 2018

(54) SYSTEM AND METHOD FOR MONITORING ABLATION SIZE

(71) Applicant: COVIDIEN LP, Mansfield, MA (US)

(72) Inventor: Joseph D. Brannan, Erie, CO (US)

(73) Assignee: Covidien LP, Mansfield, MA (US)

( * ) Notice: Subject to any disclaimer, the term of this patent is extended or adjusted under 35 U.S.C. 154(b) by 323 days.

This patent is subject to a terminal disclaimer.

(21) Appl. No.: 14/750,790

(22) Filed: Jun. 25, 2015

(65) Prior Publication Data

US 2015/0289933 A1 Oct. 15, 2015

Related U.S. Application Data

(60) Continuation of application No. 13/764,386, filed on Feb. 11, 2013, now Pat. No. 9,271,791, which is a
(Continued)

(51) Int. Cl.
*A61B 18/18* (2006.01)
*H04W 64/00* (2009.01)
(Continued)

(52) U.S. Cl.
CPC .......... *A61B 18/1815* (2013.01); *A61B 18/18* (2013.01); *H04W 64/003* (2013.01);
(Continued)

(58) Field of Classification Search
CPC ................ A61B 18/18; A61B 18/1815; A61B 2018/00577; A61B 2018/00642;
(Continued)

(56) References Cited

U.S. PATENT DOCUMENTS 4,807,620 A 2/1989 Strul et al.
5,364,392 A * 11/1994 Warner .............. A61B 18/1206
606/33

(Continued)

FOREIGN PATENT DOCUMENTS

DE 390937 C 3/1924
DE 1099658 B 2/1961
(Continued)

OTHER PUBLICATIONS

European Search Report for EP 10 01 4042 dated Feb. 18, 2011 (6 pages).
(Continued)

*Primary Examiner* — Michael Peffley

(57) ABSTRACT

A system for monitoring ablation size is provided and includes a power source including a microprocessor for executing at least one control algorithm. A microwave antenna is configured to deliver microwave energy from the power source to tissue to form an ablation zone. An ablation zone control module is in operative communication with a memory associated with the power source. The memory includes one or more data look-up tables including data pertaining to a control curve varying over time and being representative of one or more electrical parameters associated with the microwave antenna. Points along the control curve correspond to a value of the electrical parameters and the ablation zone control module triggers a signal when a predetermined threshold value of the electrical parameter(s) is measured corresponding to the radius of the ablation zone.

20 Claims, 6 Drawing Sheets

Related U.S. Application Data division of application No. 12/607,268, filed on Oct. 28, 2009, now Pat. No. 8,382,750.

(51) Int. Cl.
  *A61B 18/00* (2006.01)
  *G01S 5/02* (2010.01)

(52) U.S. Cl.
  CPC ............ *A61B 2018/00577* (2013.01); *A61B 2018/00642* (2013.01); *A61B 2018/00666* (2013.01); *A61B 2018/00684* (2013.01); *A61B 2018/00702* (2013.01); *A61B 2018/00785* (2013.01); *G01S 5/02* (2013.01)

(58) Field of Classification Search
  CPC ........... A61B 2018/00666; A61B 2018/00684; A61B 2018/00702; A61B 2018/00785
  See application file for complete search history.

(56) References Cited

U.S. PATENT DOCUMENTS

| | | |
|---|---|---|
| 5,405,346 A | 4/1995 | Grundy et al. |
| 5,683,382 A | 11/1997 | Lenihan et al. |
| 5,693,082 A | 12/1997 | Warner et al. |
| 5,957,969 A | 9/1999 | Warner et al. |
| 5,961,871 A | 10/1999 | Bible et al. |
| 6,019,757 A | 2/2000 | Scheldrup |
| 6,029,051 A | 2/2000 | Osterberg et al. |
| 6,067,475 A | 5/2000 | Graves et al. |
| 6,132,425 A | 10/2000 | Gough |
| 6,231,569 B1 | 5/2001 | Bek et al. |
| 6,287,302 B1 | 9/2001 | Berube |
| 6,500,175 B1 | 12/2002 | Gough et al. |
| 6,575,969 B1 | 6/2003 | Rittman, III et al. |
| 6,869,430 B2 * | 3/2005 | Balbierz ............ A61B 18/1206 606/41 |
| 7,749,011 B2 | 7/2010 | Arts et al. |
| 7,863,984 B1 | 1/2011 | Behnke |
| 8,035,570 B2 | 10/2011 | Prakash et al. |
| 8,038,693 B2 | 10/2011 | Allen |
| 8,059,059 B2 | 11/2011 | Bonn |
| 8,118,808 B2 | 2/2012 | Smith et al. |
| 8,182,480 B2 | 5/2012 | Huseman |
| 8,192,427 B2 | 6/2012 | Buysse |
| 8,197,473 B2 | 6/2012 | Rossetto et al. |
| 8,202,270 B2 | 6/2012 | Rossetto et al. |
| 8,211,098 B2 | 7/2012 | Paulus |
| 8,216,227 B2 | 7/2012 | Podhajsky |
| 8,221,418 B2 | 7/2012 | Prakash et al. |
| 8,235,981 B2 | 8/2012 | Prakash et al. |
| 8,251,987 B2 | 8/2012 | Willyard |
| 8,382,750 B2 | 2/2013 | Brannan |
| 2006/0289528 A1 | 12/2006 | Chiu et al. |
| 2007/0282320 A1 | 12/2007 | Buysse et al. |
| 2008/0125775 A1 | 5/2008 | Morris |
| 2008/0319434 A1 | 12/2008 | Rick et al. |
| 2009/0076409 A1 | 3/2009 | Wu et al. |
| 2009/0192507 A1 | 7/2009 | Luttich |
| 2009/0306652 A1 | 12/2009 | Buysse et al. |
| 2009/0326620 A1 | 12/2009 | Rossetto et al. |
| 2010/0030206 A1 | 2/2010 | Brannan et al. |
| 2010/0030208 A1 | 2/2010 | Manley |
| 2010/0030210 A1 | 2/2010 | Paulus |
| 2010/0045558 A1 | 2/2010 | Rossetto |
| 2010/0045559 A1 | 2/2010 | Rossetto |
| 2010/0057070 A1 | 3/2010 | Behnke et al. |
| 2010/0076422 A1 | 3/2010 | Podhajsky |
| 2010/0087808 A1 | 4/2010 | Paulus |
| 2010/0092939 A1 | 4/2010 | Belous et al. |
| 2010/0094272 A1 | 4/2010 | Rossetto et al. |
| 2010/0094273 A1 | 4/2010 | Rossetto et al. |
| 2010/0097284 A1 | 4/2010 | Brannan et al. |
| 2010/0256624 A1 | 10/2010 | Brannan et al. |
| 2010/0262134 A1 | 10/2010 | Jensen et al. |
| 2010/0286681 A1 | 11/2010 | Podhajsky |
| 2010/0286683 A1 | 11/2010 | Podhajsky |
| 2010/0305559 A1 | 12/2010 | Brannan et al. |
| 2010/0305560 A1 | 12/2010 | Peterson |
| 2010/0321192 A1 | 12/2010 | Brannan |
| 2010/0321257 A1 | 12/2010 | Brannan |
| 2010/0331834 A1 | 12/2010 | Peterson et al. |
| 2011/0034913 A1 | 2/2011 | Brannan |
| 2011/0034917 A1 | 2/2011 | Brannan |
| 2011/0034919 A1 | 2/2011 | DeCarlo |
| 2011/0040300 A1 | 2/2011 | Brannan |
| 2011/0054458 A1 | 3/2011 | Behnke |
| 2011/0054459 A1 | 3/2011 | Peterson |
| 2011/0060325 A1 | 3/2011 | Bonn |
| 2011/0060326 A1 | 3/2011 | Smith et al. |
| 2011/0066144 A1 | 3/2011 | Bonn et al. |
| 2011/0071511 A1 | 3/2011 | Brannan et al. |
| 2011/0071512 A1 | 3/2011 | Behnke, II et al. |
| 2011/0071582 A1 | 3/2011 | Willyard et al. |
| 2011/0073594 A1 | 3/2011 | Bonn |
| 2011/0077632 A1 | 3/2011 | Rossetto |
| 2011/0077633 A1 | 3/2011 | Bonn et al. |
| 2011/0077634 A1 | 3/2011 | Brannan |
| 2011/0077635 A1 | 3/2011 | Bonn |
| 2011/0077636 A1 | 3/2011 | Brannan et al. |
| 2011/0077637 A1 | 3/2011 | Brannan |
| 2011/0077638 A1 | 3/2011 | Brannan |
| 2011/0077639 A1 | 3/2011 | Brannan et al. |
| 2011/0098695 A1 | 4/2011 | Brannan |
| 2011/0098696 A1 | 4/2011 | Brannan |
| 2011/0098697 A1 | 4/2011 | Brannan |
| 2011/0118721 A1 | 5/2011 | Brannan |
| 2011/0118731 A1 | 5/2011 | Ladtkow |

FOREIGN PATENT DOCUMENTS

| | | |
|---|---|---|
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |

(56) References Cited

FOREIGN PATENT DOCUMENTS

| | | |
|---|---|---|
| EP | 0 556 705 A1 | 8/1993 |
| EP | 0 558 429 A1 | 9/1993 |
| EP | 0 836 868 A2 | 4/1998 |
| EP | 1055399 | 11/2000 |
| EP | 1080694 | 3/2001 |
| EP | 1159926 A3 | 3/2003 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09010223 A | 1/1997 |
| JP | Hei10-243947 | 9/1998 |
| JP | 11244298 A | 9/1999 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| JP | 2001-510702 | 8/2001 |
| JP | 2007-532024 | 11/2007 |
| SU | 166452 | 1/1965 |
| SU | 401367 A1 | 10/1973 |
| SU | 727201 | 4/1980 |
| WO | 2004086995 A1 | 10/2004 |
| WO | 2008/090484 A2 | 7/2008 |

OTHER PUBLICATIONS

European Search Report EP 10 01 4081 dated Mar. 4, 2011.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic .RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.

B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman et al., "Laparoscopic Intestinal Resection With the LigaSure.TM. Vessel Sealing System: A Case Report" Innovations That Work, Feb. 2002.

(56) References Cited

OTHER PUBLICATIONS

Humphries Jr. et al., "Finite Element Codes to Model Electrical Heating and Non Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2007.
European Search Report EP 07015601.3 dated Jan. 4, 2007.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08011282 dated Aug. 14, 2009.
European Search Report EP 08011705 dated Aug. 20, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08169973.8 dated Apr. 6, 2009.
European Search Report EP 09156861.8 dated Aug. 4, 2009.
European Search Report EP 09161502.1 dated Sep. 2, 2009.
European Search Report EP 09166708 dated Oct. 15, 2009.
Office Action for Japanese Application No. 2014-258573 dated Nov. 17, 2015.
Gazette of Japanese Patent Application Laid-Open 2009-528 with English Abstract.
Gazette of Japanese Unexamined Patent Application, First Publication No. H02-185267 with English Abstract.
Gazette of Japanese Patent Application Laid-Open No. H09-117456 with English Abstracf.
Gazette of Japanese Patent Application Laid-Open No. 2001-37775 with English Abstract.
Japanese Office Action for Application No. 2016-056456 dated Dec. 6, 2016.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Jul. 25, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
International Search Report PCT/US98/18640 dated Jan. 29, 1998.

(56) References Cited

OTHER PUBLICATIONS

International Search Report PCT/US98/23950 dated Jan. 14, 1998.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2004.
International Search Report PCT/US05/36168 dated Aug. 28, 2006.
International Search Report PCT/US08/052460 dated Apr. 24, 2008.
International Search Report PCT/US09/31658 dated Mar. 11, 2009.
European Search Report; Application No. EP 10 01 4080 dated Mar. 4, 2011.
European Search Report for European Application No. 11001596.3 dated Jun. 27, 2011.
U.S. Appl. No. 08/483,742, filed Jun. 7, 1995, Roger A. Stern.
U.S. Appl. No. 08/136,098, filed Oct. 14, 1993, Roger A. Stern.
Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, pp. 205-210.
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radial, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure. TM. Vessel Sealing System and LigaSure.TM. Atlas 20 cm Open Instrument" Innovations That Work, Jun. 2003.
Muller et al., "Extended Left Hemicolectomy Using the LigaSure. TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.

Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817.cndot.825.
Urologix, Inc.—Medical Professionals: Targis.TM. Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.

(56) References Cited

OTHER PUBLICATIONS

W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 03721482 dated Feb. 6, 2006.
European Search Report EP 04009964 dated Jul. 28, 2004.

* cited by examiner

SYSTEM AND METHOD FOR MONITORING ABLATION SIZE

CROSS-REFERENCE TO RELATED APPLICATIONS

This application is a continuation application of U.S. patent application Ser. No. 13/764,386, filed on Feb. 11, 2013, now U.S. Pat. No. 9,271,791, which is a divisional application of U.S. patent application Ser. No. 12/607,268, filed on Oct. 28, 2009, now U.S. Pat. No. 8,382,750, the entire contents of all of which are incorporated by reference herein.

BACKGROUND

Technical Field

The present disclosure relates to systems and methods that may be used in tissue ablation procedures. More particularly, the present disclosure relates to systems and methods for monitoring ablation size during tissue ablation procedures in real-time.

Background of Related Art

In the treatment of diseases such as cancer, certain types of cancer cells have been found to denature at elevated temperatures (which are slightly lower than temperatures normally injurious to healthy cells). These types of treatments, known generally as hyperthermia therapy, typically utilize electromagnetic radiation to heat diseased cells to temperatures above 41° C. while maintaining adjacent healthy cells at lower temperatures where irreversible cell destruction will not occur. Procedures utilizing electromagnetic radiation to heat tissue may include ablation of the tissue.

Microwave ablation procedures, e.g., such as those performed for menorrhagia, are typically done to ablate the targeted tissue to denature or kill the tissue. Many procedures and types of devices utilizing electromagnetic radiation therapy are known in the art. Such microwave therapy is typically used in the treatment of tissue and organs such as the prostate, heart, and liver.

One non-invasive procedure generally involves the treatment of tissue (e.g., a tumor) underlying the skin via the use of microwave energy. The microwave energy is able to non-invasively penetrate the skin to reach the underlying tissue. However, this non-invasive procedure may result in the unwanted heating of healthy tissue. Thus, the non-invasive use of microwave energy requires a great deal of control.

Currently, there are several types of systems and methods for monitoring ablation zone size. In certain instances, one or more types of sensors (or other suitable devices) are operably associated with the microwave ablation device. For example, in a microwave ablation device that includes a monopole antenna configuration, an elongated microwave conductor may be in operative communication with a sensor exposed at an end of the microwave conductor. This type of sensor is sometimes surrounded by a dielectric sleeve.

Typically, the foregoing types of sensor(s) are configured to function (e.g., provide feedback to a controller for controlling the power output of a power source) when the microwave ablation device is inactive, i.e., not radiating. That is, the foregoing sensors do not function in real-time. Typically, the power source is powered off (or pulsed off) when the sensors are providing feedback (e.g., tissue temperature) to the controller and/or other device(s) configured to control the power source.

SUMMARY

The present disclosure provides a system for monitoring ablation size in real-time. The system includes a power source including a microprocessor for executing one or more control algorithms. A microwave antenna is configured to deliver microwave energy from the power source to tissue to form an ablation zone. An ablation zone control module is in operative communication with a memory associated with the power source. The memory includes one or more data look-up tables including data pertaining to a control curve varying over time and being representative of one or more electrical parameters associated with the microwave antenna. Points along the control curve correspond to a value of the electrical parameters and the ablation zone control module triggers a signal when a predetermined threshold value of the electrical parameter(s) is measured corresponding to the radius of the ablation zone.

The present disclosure also provides a microwave antenna adapted to connect to a power source configured for performing an ablation procedure. The microwave antenna includes a radiating section configured to deliver microwave energy from a power source to tissue to form an ablation zone. An ablation zone control module in operative communication with a memory associated with the power source. The memory includes one or more data look-up tables including data pertaining to a control curve varying over time and being representative of one or more electrical parameter(s) associated with the microwave antenna. Points along the control curve correspond to a value of the electrical parameter(s) and the ablation zone control module triggers a signal when a predetermined threshold value of the at least one electrical parameter is measured corresponding to the radius of the ablation zone.

The present disclosure also provides a method for monitoring temperature of tissue undergoing ablation. The method includes an initial step of transmitting microwave energy from a power source to a microwave antenna to form a tissue ablation zone. A step of the method includes monitoring reflected power associated with the microwave antenna as the tissue ablation zone forms. A step of the method includes communicating a control signal to the power source when a predetermined reflected power is reached at the microwave antenna. Adjusting the amount of microwave energy from the power source to the microwave antenna is another step of the method.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
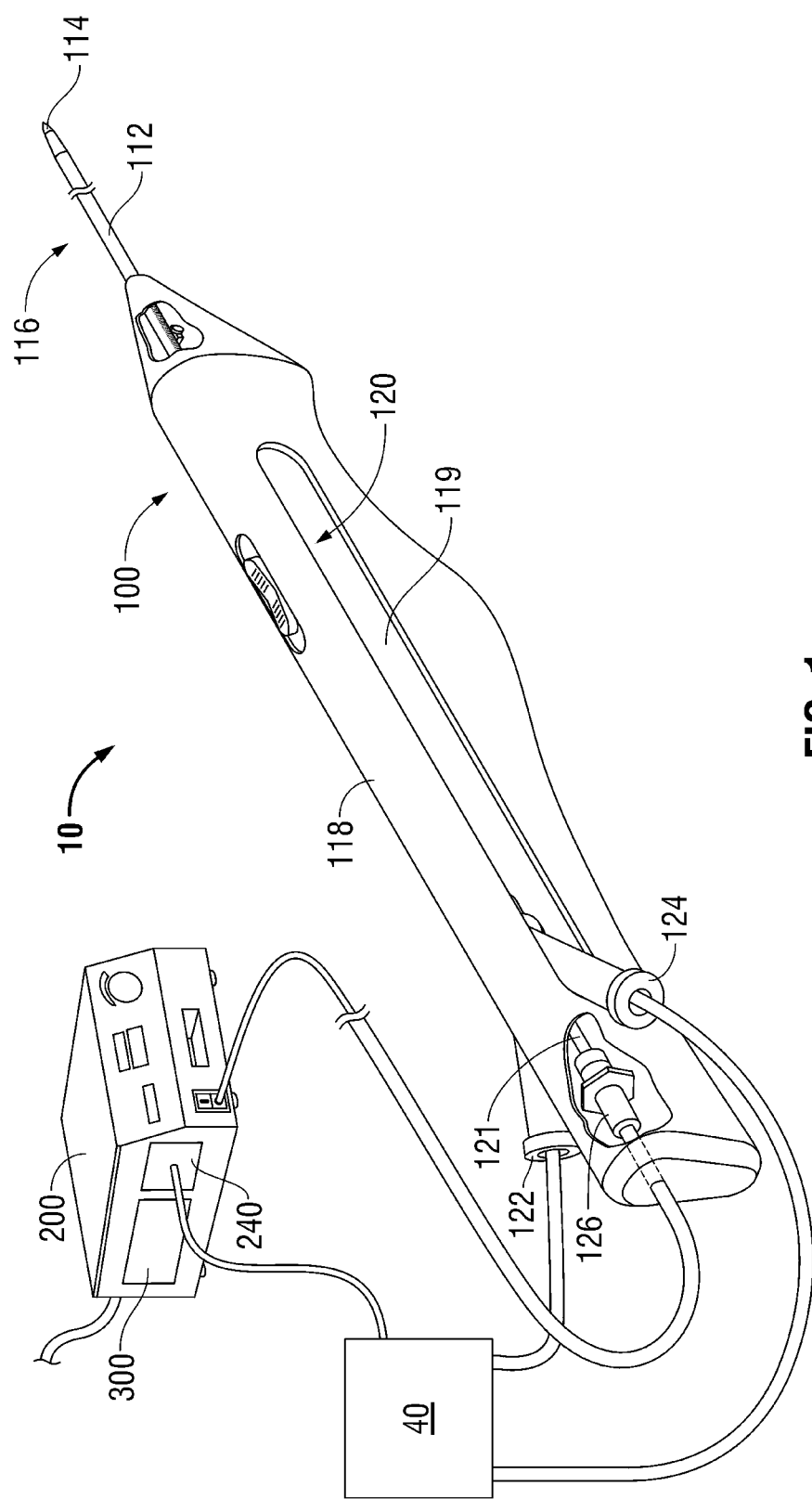
FIG. 1 is a perspective view of a system for monitoring ablation size according to an embodiment of the present disclosure.

Embodiments of the presently disclosed system and method are described in detail with reference to the drawing figures wherein like reference numerals identify similar or identical elements. As used herein and as is traditional, the term "distal" refers to the portion which is furthest from the user and the term "proximal" refers to the portion that is closest to the user. In addition, terms such as "above", "below", "forward", "rearward", etc. refer to the orientation of the figures or the direction of components and are simply used for convenience of description.

Referring now to FIG. 1, a system for monitoring ablation size is designated 10. The system 10 includes a microwave antenna 100 that is adapted to connect to an electrosurgical power source, e.g., an RF and/or microwave (MW) generator 200 that includes or is in operative communication with one or more controllers 300 and, in some instances, a fluid supply pump 40. Briefly, microwave antenna 100 includes an introducer 116 having an elongated shaft 112 and a radiating or conductive section or tip 114 operably disposed within elongated shaft 112, a cooling assembly 120 having a cooling sheath 121, a handle 118, a cooling fluid supply 122 and a cooling fluid return 124, and an electrosurgical energy connector 126. Connector 126 is configured to connect the microwave antenna 100 to the electrosurgical power source 200, e.g., a generator or source of radio frequency energy and/or microwave energy, and supplies electrosurgical energy to the distal portion of the microwave antenna 100. Conductive tip 114 and elongated shaft 112 are in electrical communication with connector 126 via an internal coaxial cable 126a (see FIG. 3A, for example) that extends from the proximal end of the microwave antenna 100 and includes an inner conductor tip that is operatively coupled to a radiating section 138 operably disposed within the shaft 112 and adjacent the conductive or radiating tip 114 (see FIG. 3A, for example). As is common in the art, internal coaxial cable 126a is includes a dielectric material and an outer conductor surrounding each of the inner conductor tip and dielectric material. A connection hub (not shown) disposed at a proximal end of the microwave antenna 100 operably couples connector 126 to internal coaxial cable 126a, and cooling fluid supply 122 and a cooling fluid return 124 to a cooling assembly 120. Radiating section 138 by way of conductive tip 114 (or in certain instances without conductive tip 114) is configured to deliver radio frequency energy (in either a bipolar or monopolar mode) or microwave energy (having a frequency from about 500 MHz to about 10 GHz) to a target tissue site. Elongated shaft 112 and conductive tip 114 may be formed of suitable conductive material including, but not limited to copper, gold, silver or other conductive metals having similar conductivity values. Alternatively, elongated shaft 112 and/or conductive tip 114 may be constructed from stainless steel or may be plated with other materials, e.g., other conductive materials, such as gold or silver, to improve certain properties, e.g., to improve conductivity, decrease energy loss, etc. In an embodiment, the conductive tip may be deployable from the elongated shaft 112. In one particular embodiment, microwave antenna 100 may include an introducer 116 having an elongated shaft 112 and a tip 114 that is non-conductive. In this instance, the tip 114 may be made from a non-conductive material such as, for example, ceramic, plastic, etc.

Figure 2:
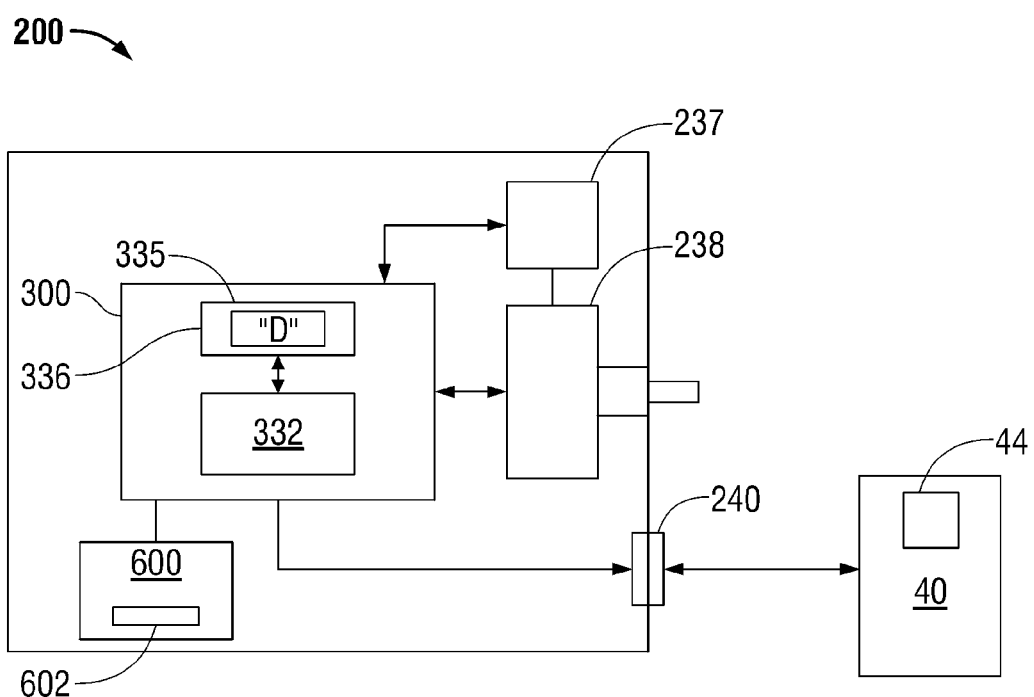
FIG. 2 is a functional block diagram of a power source for use with the system depicted in FIG. 1.

With reference to FIG. 2, a schematic block diagram of the generator 200 is illustrated. The generator 200 includes a controller 300 having one or more modules (e.g., an ablation zone control module 332 (AZCM 332), a power supply 237 and a microwave output stage 238). In this instance, generator 200 is described with respect to the delivery of microwave energy. The power supply 237 provides DC power to the microwave output stage 238 which then converts the DC power into microwave energy and delivers the microwave energy to the radiating section 138 of the microwave antenna 100. The controller 300 may include analog and/or logic circuitry for processing sensed values provided by the AZCM 332 and determining the control signals that are sent to the generator 200 and/or supply pump 40 via a microprocessor 335. The controller 300 (or component operably associated therewith) accepts one or more measured signals indicative of reflected power $P_r$ associated with the microwave antenna 100 when the microwave antenna is radiating energy.

One or more modules e.g., AZCM 332, of the controller 300 analyzes the measured signals and determines if a threshold reflected power $P_r$, e.g., $P_{r1}$ has been met. If the threshold reflected power $P_{r1}$ has been met, then the AZCM 332, a microprocessor 335 and/or the controller instructs the generator 200 to adjust the microwave output stage 238 and/or the power supply 237 accordingly. Additionally, the controller 300 may also signal the supply pump to adjust the amount of cooling fluid to the microwave antenna 100 and/or the surrounding tissue. The controller 200 includes microprocessor 335 having memory 336 which may be volatile type memory (e.g., RAM) and/or non-volitile type memory (e.g., flash media, disk media, etc.). In the illustrated embodiment, the microprocessor 335 is in operative communication with the power supply 237 and/or microwave output stage 238 allowing the microprocessor 335 to control the output of the generator 300 according to either open and/or closed control loop schemes. The microprocessor 335 is capable of executing software instructions for processing data received by the AZCM 332, and for outputting control signals to the generator 300 and/or supply pump 40, accordingly. The software instructions, which are executable by the controller 300, are stored in the memory 336.

One or more electrical properties (e.g., voltage, current, power, impedance, etc.) associated with a signal (or pulse) generated by the generator 200 may be monitored and measured. More particularly, electrical properties associated with a forward and reflected portion of the signal generated by the generator 200 is monitored and measured. For example, in one particular embodiment, forward and reflected power, $P_f$ and $P_r$, respectively, of a signal for ablating tissue is measured by the AZCM 332, controller 300, microprocessor 337 or other suitable module associated with the generator 200 and/or controller 200.

Figure 4A:
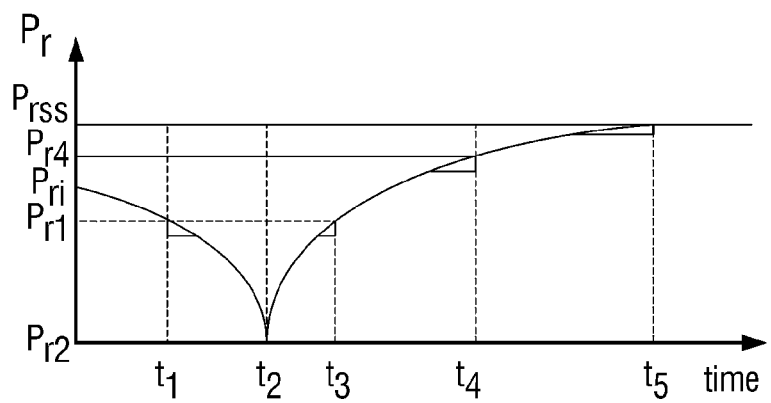
FIG. 4A is a graphical representation of a reflected power ($P_r$) versus time (t) curve.
Figure 4B:
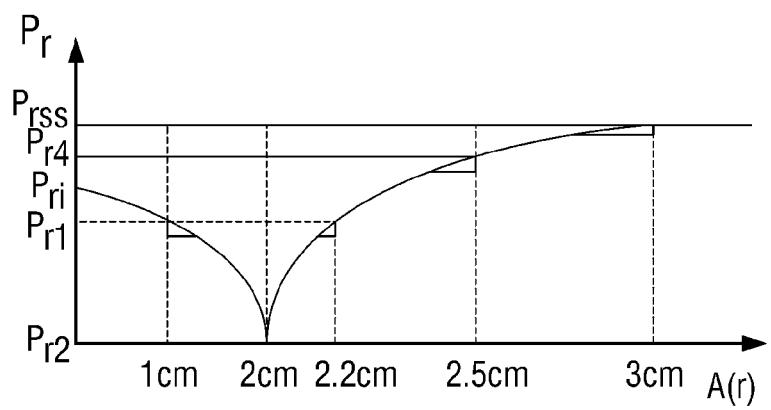
FIG. 4B a graphical representation of a corresponding reflected power ($P_r$) versus ablation radii (Ar) curve.

One or more control algorithms for predicting tissue ablation size is implemented by the controller 300. More particularly, the concept of correlating reflected power $P_r$ associated with a particular microwave antenna, e.g., the microwave antenna 100, with an ablation zone "A" having a radius "r" may be used to indicate tissue death or necrosis. More particularly, reflected power $P_r$ associated with the microwave antenna 100 varies over the course of an ablation cycle due to tissue complex permittivity changes caused by temperature increase (see FIGS. 4A and 4B, for example). A relationship of reflected power $P_r$ as a function of time is represented by a control curve illustrated in FIG. 4A. Likewise, a relationship of reflected power $P_r$ as a function of ablation size is represented by a control curve illustrated in FIG. 4B. The control curves represented in FIGS. 4A and 4B are based on model functions $f(t)$ and known measured values of reflected power $P_r$ that have been taken during an ablation procedure performed with the microwave antenna 100, controller 300 and/or generator 200. In accordance with the present disclosure, the control curves depicted in FIGS. 4A and 4B (and/or equations mathematically associated therewith) may be utilized to calculate and/or verify when a specified threshold reflected power $P_r$ (e.g., reflected powers $P_{r1-ss}$) within a specified time range (e.g., $t_1$-$t_{ss}$) not exceeding $t_{ss}$, i.e., time when the microwave antenna 100 and ablated tissue is at a steady-state condition, see FIG. 4A or FIG. 4B, for example. The significance of when the microwave antenna 100 and ablated tissue is at a steady-state condition is described in greater detail below.

With reference now to FIGS. 4A and 4B, initially, an impedance mismatch between the microwave antenna 100 and tissue is present when the microwave antenna 100 is inserted into uncooked tissue. This impedance mismatch is due to the 50 ohm impedance associated with the internal cable 126a not matching the impedance of the radiating section 118 and/or conductive tip 114. The impedance mismatch results in a non-zero reflected power $P_{ri}$, at the beginning of the ablation procedure, see FIGS. 4A and 4B, for example. During the course of the ablation procedure, tissue in a "near field" heats up resulting in a decrease in reflected power $P_r$ (in a non-linear rate) (see FIG. 4A for example) until an optimal impedance match between the microwave antenna 100 and tissue is reached (see FIG. 4A at a time equal to time $t_2$ in combination with FIG. 4B at an ablation size having a radius "r" equal to 2 cm). That is, the total impedance $Z_t$ of the microwave antenna 100 and tissue in the "near field" is approximately equal to 50 ohms. The microwave antenna 100 and tissue in the "near field" remain at this optimal impedance match for a brief period of time. At a time after time $t_2$, the microwave antenna 100 and tissue in the near field diverge from the optimal impedance match (in a non-linear rate). Ultimately, when the microwave antenna 100 has heated tissue to a maximum attainable temperature, an ablation zone "A" having a corresponding radius "r" (e.g., $r_{ss}$) is formed (see FIG. 3A in combination with FIGS. 4A and 4B, for example). At this maximum temperature, a dielectric constant and conductivity associated with the ablated tissue reach a steady-state condition (this steady-state condition occurs at time $t_{ss}$) that corresponds to a steady-state reflected power $P_{rss}$ (hereinafter referred to simply as $P_{rss}$) associated with the microwave antenna 100. That is, because the ablated tissue is in a "near field" of the microwave antenna 100, the ablated tissue essentially becomes part of the microwave antenna 100. Accordingly, when a dielectric constant and conductivity associated with the ablated tissue reaches a steady-state condition, the reflected power $P_r$ at the microwave antenna 100 also reaches a steady-state condition, e.g., $P_{rss}$, FIG. 4A.

As noted above, the foregoing control algorithm includes one or more model functions $f(t)$ that are representative of the model curves illustrated in FIGS. 4A and 4B. The model functions $f(t)$, model curves depicted in FIGS. 4A and 4B, and/or known measured values of reflected power $P_r$, are utilized to obtain information relevant to the reflected power $P_r$ such that real-time monitoring of an ablation zone may be achieved. More particularly, a measurement of a slope of a tangent line at a point along either of the control curves (e.g., curve illustrated in FIG. 4A) is equal to a derivative ($dP_r/dt$) of the curve at that point. The calculation of the derivative at a particular point along the curve(s) provides information pertinent to the reflected power $P_r$. More particularly, a rate of change of reflected power $P_r$ with respect to time and, more particularly, to a vector quantity of the rate of change of the reflected power $P_r$ (i.e., direction (positive or negative) and magnitude of the rate of change) is calculated from the control curve(s) depicted in FIGS. 4A-4C. This rate of change associated with reflected power $P_r$ with respect to time may be utilized, for example, to distinguish between a rise and fall of the reflected power $P_r$. More particularly, points taken along the control curves depicted in FIGS. 4A and 4B correspond to values of reflected power $P_r$, e.g., reflected powers $P_{r1}$ and $P_{r3}$, which correspond to ablation zones "A" having radii "r," e.g., radii $r_1$ and $r_3$, at corresponding times t, e.g., times $t_1$ and $t_3$. It should be noted that a value of reflected power, e.g., $P_{r1}$, corresponds to more than one radius, e.g., $r_1$ and $r_3$ of an ablation zone.

More particularly, the representative control curve of reflected power $P_r$ depicted in FIGS. 4A and 4B illustrates reflected power $P_r$ having an initial value, e.g., $P_i$, at the beginning of an ablation procedure. The reflected power $P_r$ decreases until the reflected power $P_r$ is approximately equal to zero, i.e., when the total impedance of microwave antenna 100 and tissue in a "near field" is approximately equal to 50 ohms. The reflected power $P_r$ increases at a time after time $t_2$ when the total impedance of microwave antenna 100 and tissue in the "near field" is not equal to 50 ohms. Accordingly, a measure of reflected power $P_r$ taken along the control curve provides one or more numerical values of the reflected power $P_r$ that is indicative of one or more ablation zones "A" having corresponding radii "r." For example, a measure of the reflected power $P_r$, e.g., $P_{r1}$, at time $t_1$ corresponds to an ablation zone "A" having a radius $r_1$ that is approximately equal to 1 cm, see FIGS. 4A and 4B collectively. Likewise, a measure of the reflected power $P_r$, e.g., $P_{r1}$, at time $t_3$ also corresponds to an ablation zone "A" having a radius $r_3$ that is approximately equal to 2.2 cm, see FIGS. 4A and 4B collectively.

In accordance with the present disclosure, samples of a derivative taken at selective points along the control curve (e.g., points corresponding to radii $r_1$ and $r_3$ and/or points corresponding to times $t_1$ and $t_3$) provide information pertaining to the precise location (e.g., rise or fall portions of the control curve) of the reflected power $P_r$ with respect to the control curve.

Figure 4C:
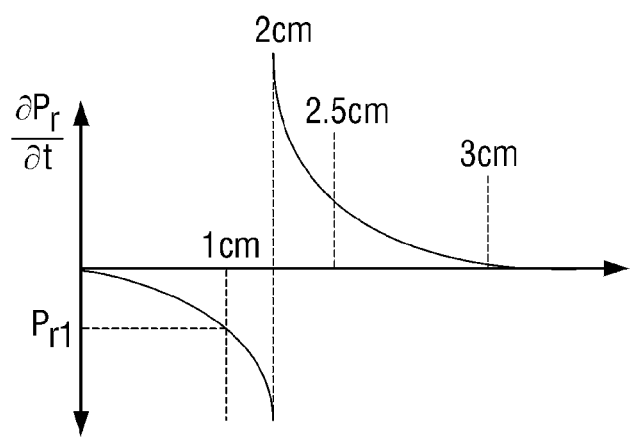
FIG. 4C is a graphical representation of the derivative ($dP_r/dt$) of the reflected power (Pr) versus time (t) curve.

More particularly, and for example, a derivative taken at a point along the control curve at time $t_1$ when the reflected power $P_r$ is approximately equal to $P_{r1}$ is negative because the slope of the reflected power $P_r$ is declining, as best seen in FIG. 4C. In this instance, reflected power $P_{r1}$ may be thought of as having and is assigned a negative value indicating to one or more modules, e.g., AZCN 332, associated with the controller 300 and/or generator 200 that this value of the reflected power $P_{r1}$ is indicative of and corresponds to an ablation zone "A" having a radius $r_1$. Similarly, samples of a derivative taken at a point along the control curve at time $t_3$ when the reflected power $P_r$ is approximately equal to $P_{r1}$ is positive because the slope of the reflected power $P_r$ is increasing, as best seen in FIG. 4C. In this instance, reflected power $P_{r1}$ may be thought of as having and is assigned a positive value indicating to one or more modules, e.g., AZCN 332, associated with the controller 300 and/or generator 200 that this value of the reflected power $P_{r1}$ is indicative of and corresponds to an ablation zone "A" having a radius $r_3$.

Implementing a control algorithm that utilizes a calculation of a derivative taken at a point on the control curve facilitates in determining the precise size of the ablation zone "A." That is, one or more modules, e.g., AZCM 332, associated with the controller 300 and generator 200 is capable of distinguishing between which ablation zone radius "r," e.g., radius $r_1$ or $r_2$, corresponds to the reflected power $P_r$, e.g., measured reflected power $P_{r1}$. Moreover, in the instance where multiple ablation zones "A" are located adjacent to one another, tissue impedance of uncooked tissue at a near field of an ablation zone "A" may effect a reflected power $P_r$ measurement. More particularly, tissue impedance of uncooked tissue at the near field may be slightly higher or lower (depending on a specific adjacent ablation zone "A"), which, in turn, may cause the reflected power $P_r$ to be higher or lower at the beginning of an ablation procedure then is expected. Thus, in the instance where the initial reflected power $P_i$ is approximately equal to $P_{r4}$, a calculation of the derivative taken at a point on the control curve indicates that the microwave antenna 100 is positioned adjacent cooked or ablated tissue. That is, the initial positive value of $P_{r4}$ indicates that the reflected power $P_r$ is increasing, and, thus, a steady-state condition is approaching, i.e., a calculation of the derivative indicates that the measured reflected power $P_r$ is in the rising portion of the control curve and the reflected power $P_r$ will not approach zero, i.e., a point on the control curve where the total impedance associated with the microwave antenna 100 and tissue adjacent the near field is approximately equal to 50 ohms.

Figure 3A:
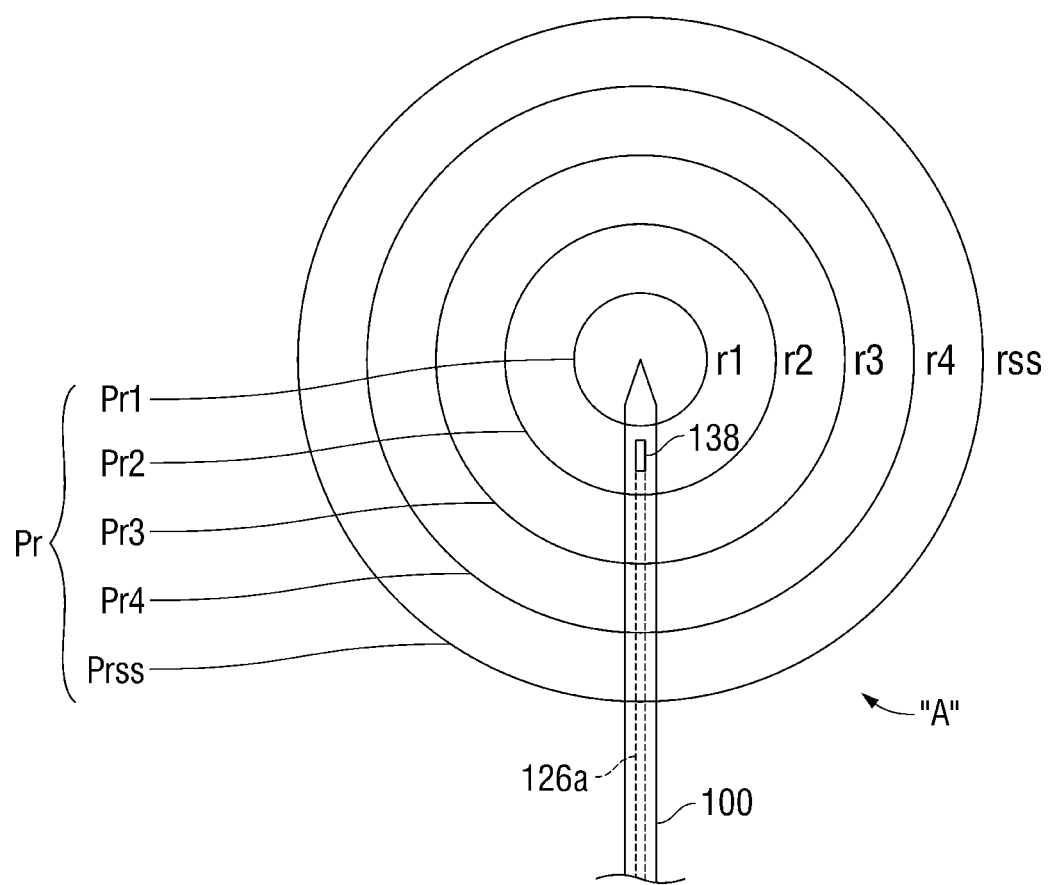
FIG. 3A is a schematic, plan view of the tip of a microwave antenna depicted in FIG. 1 illustrating radial ablation zones having a spherical configuration.
Figure 3B:
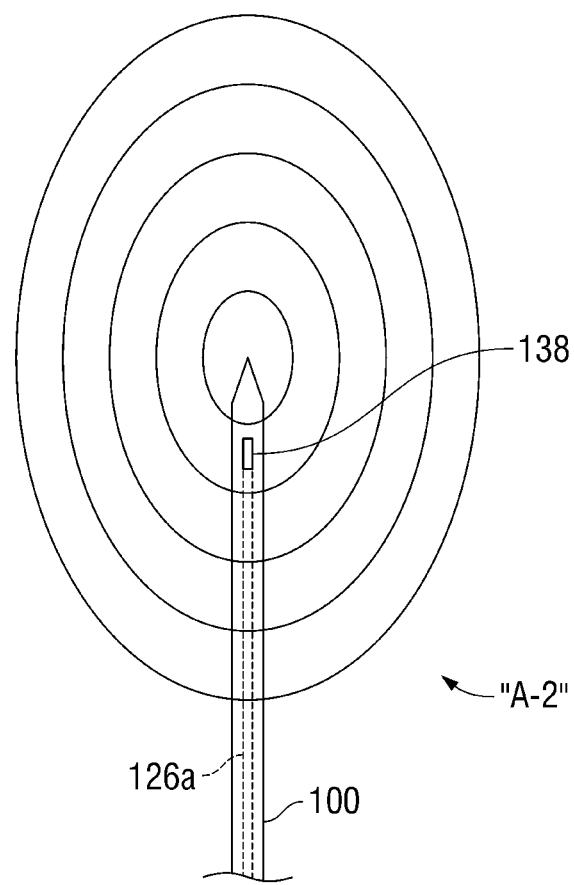
FIG. 3B is a schematic, plan view of the tip of a microwave antenna depicted in FIG. 1 illustrating radial ablation zones having an ellipsoidal configuration.

The microwave antenna 100 of the present disclosure may be configured to create an ablation zone "A" having any suitable configuration (e.g., a width "w" and a length "l"), such as, for example, spherical (FIG. 3A), hemispherical, ellipsoidal (FIG. 3B where the ablation zone is designated "A-2"), and so forth. In one particular embodiment, microwave antenna 100 is configured to create an ablation zone "A" that is spherical (FIG. 3A). As noted above, when the microwave antenna 100 has heated tissue in the "near field" to a maximum temperature, a dielectric constant and conductivity associated with the ablated tissue reaches a steady-state that corresponds to a steady-state reflected power $P_{rss}$ associated with the microwave antenna 100. Correlating the $P_{rss}$ associated with the microwave antenna 100 with the ablated tissue (i.e., ablated tissue, where the dielectric constant and conductivity are in a steady-state condition), indicates a specific size (e.g., radius $r_{ss}$) and shape (e.g., spherical) of the ablation zone "A." Thus, a measure of $P_{rss}$ associated with the microwave antenna 100 corresponds to an ablation zone "A" having a radius r, e.g., $r_{ss}$. The control algorithm of the present disclosure uses known steady-state reflected powers associated with specific microwave antennas at specific radii to predict an ablation size. That is, reflected powers $P_r$, e.g., $P_{rss}$, associated with a specific microwave antenna, e.g., microwave antenna 100, and corresponding radius, e.g., $r_{ss}$, are compiled into one or more look-up tables "D" and are stored in memory, e.g., memory 336, accessible by the microprocessor 335 and/or the AZCM 332. Thus, when a measured reflected power for a specific microwave antenna, e.g., microwave antenna 100, reaches $P_{rss}$ one or more modules, e.g. AZCM 332, associated with the controller 300, commands the controller 200 to adjust the power output to the microwave antenna 100 accordingly. This combination of events will provide an ablation zone "A" with a radius approximately equal to $r_{ss}$.

In an embodiment, for a given microwave antenna, e.g., microwave antenna 100, reflected power measurements may be taken at times prior to $t_{ss}$, e.g., times $t_1$-$t_4$. In this instance, reflected powers, e.g., $P_{r1}$-$P_{r4}$, associated with the microwave antenna 100 may be correlated with an ablation zone "A" defined by a plurality of concentric ablation zones having radii $r_1$-$r_4$ (collectively referred to as radii "r") when measured from the center of the ablation zone "A." More particularly, the reflected powers $P_{r1}$-$P_{r4}$ and corresponding radii "r" may be correlated with each other in a manner as described above with respect to $P_{rss}$ and $r_{ss}$ (see FIG. 3A in combination with FIGS. 4A and 4B, for example). In this instance, when specific reflected power, e.g., $P_3$, is met one or more modules, e.g. AZCM 332, associated with the controller 300, commands the controller 200 to adjust the power output to the microwave antenna 100 accordingly.

It should be noted, that a reflected power $P_r$ associated with a microwave antenna 100 may vary for a given microwave antenna. Factors that may contribute to a specific reflected power $P_r$ for a given microwave antenna include but are not limited to: dimensions associated with the microwave antenna (e.g., length, width, etc.); type of material used to manufacture the microwave antenna (or portion associated therewith, e.g., a radiating section) such as copper, silver, etc; and the configuration of the radiating section (e.g., dipole, monopole, etc.) and/or a conductive tip (e.g., sharp, blunt, curved, etc) associated with the microwave antenna. Other factors that may contribute to a specific reflected power $P_r$ for a given microwave antenna may include, for example, type of microwave antenna (e.g., microwave antenna configured for use in treating lung, kidney, liver, etc.), type of tissue being treated (e.g., lung, kidney, liver, heart etc.), tumor size, and so on.

AZCM 332 may be a separate module from the microprocessor 335, or AZCM 332 may be included with the microprocessor 335. In an embodiment, the AZCM 332 may be operably disposed on the microwave antenna 100. The AZCM 332 may include control circuitry that receives information from one or more control modules and/or one or more impedance sensors (not shown), and provides the information to the controller 300 and/or microprocessor 335. In this instance, the AZCM 332, microprocessor 335 and/or controller 300 may access look-up table "D" and confirm that a particular reflected power (e.g., $P_{rss}$) associated with microwave assembly 100 corresponds to a specific ablation zone (e.g., specific ablation zone having a radius $r_{ss}$) has been met and, subsequently, instruct the generator 200 to adjust the amount of microwave energy being delivered to the microwave antenna. In one particular embodiment, look-up table "D" may be stored in a memory storage device (not shown) associated with the microwave antenna 100. More particularly, a look-up table "D" may be stored in a memory storage device operatively associated with handle 118 and/or connector 126 of the microwave antenna 100 and may be downloaded, read and stored into microprocessor 335 and/or memory 336 and, subsequently, accessed and utilized in a manner described above; this would do away with reprogramming the generator 200 and/or controller 300 for a specific microwave antenna. The memory storage device may also be configured to include information pertaining to the microwave antenna 100. Information, such as, for example, the type of microwave antenna, the type of tissue that the microwave antenna is configured to treat, the type of ablation zone desired, etc. may be stored into the storage device associated with the microwave antenna. In this instance, for example, generator 200 and/or controller 300 of system 10 may be adapted for use with a microwave antenna configured to create an ablation zone, e.g. ablation zone "A-2," different from that of microwave antenna 100 that is configured to create an ablation zone "A."

In the embodiment illustrated in FIGS. 1-4, the generator is shown operably coupled to fluid supply pump 40. The supply pump 40 is, in turn, operably coupled to the supply tank 44. In embodiments, the microprocessor 335 is in operative communication with the supply pump 40 via one or more suitable types of interfaces, e.g., a port 240 operatively disposed on the generator 200, which allows the microprocessor 335 to control the output of a cooling fluid from the supply pump 40 to the microwave antenna 100 according to either open and/or closed control loop schemes. The controller 300 may signal the supply pump 40 to control the output of the cooling fluid from the supply tank 44 to the microwave antenna 100. In this way, cooling fluid 42 is automatically circulated to the microwave antenna 100 and back to the supply pump 40. In certain embodiments, a clinician may manually control the supply pump 40 to cause cooling fluid 42 to be expelled from the microwave antenna 100 into and/or proximate the surrounding tissue.

Operation of system 10 is now described. In the description that follows, it is assumed that losses associated with the connector 126 and/or cable 162a are negligible and, thus, are not needed in calculating and/or determining a reflected power of the microwave antenna 100 adjacent the ablation zone during the ablation procedure. Initially, microwave antenna 100 is connected to generator 200. In one particular embodiment, one or more modules, e.g., AZCM 332, associated with the generator 200 and/or controller 300 reads and/or downloads data from a storage device associated with the antenna 100, e.g., the type of microwave antenna, the type of tissue that is to be treated, etc. Microwave antenna 100 may then be positioned adjacent tissue (FIG. 3A). Thereafter, generator 200 may be activated supplying microwave energy to radiating section 138 of the microwave antenna 100 such that the tissue may be ablated. During tissue ablation, when a predetermined reflected power, e.g., $P_{rss}$, at the microwave antenna 100 is reached, the AZCM 332 instructs the generator 200 to adjust the microwave energy accordingly. In the foregoing sequence of events the AZCM 332 functions in real-time controlling the amount of microwave energy to the ablation zone such that a uniform ablation zone of suitable proportion (e.g., ablation zone "A" having a radius $r_{ss}$) is formed with minimal or no damage to adjacent tissue.

Figure 5:
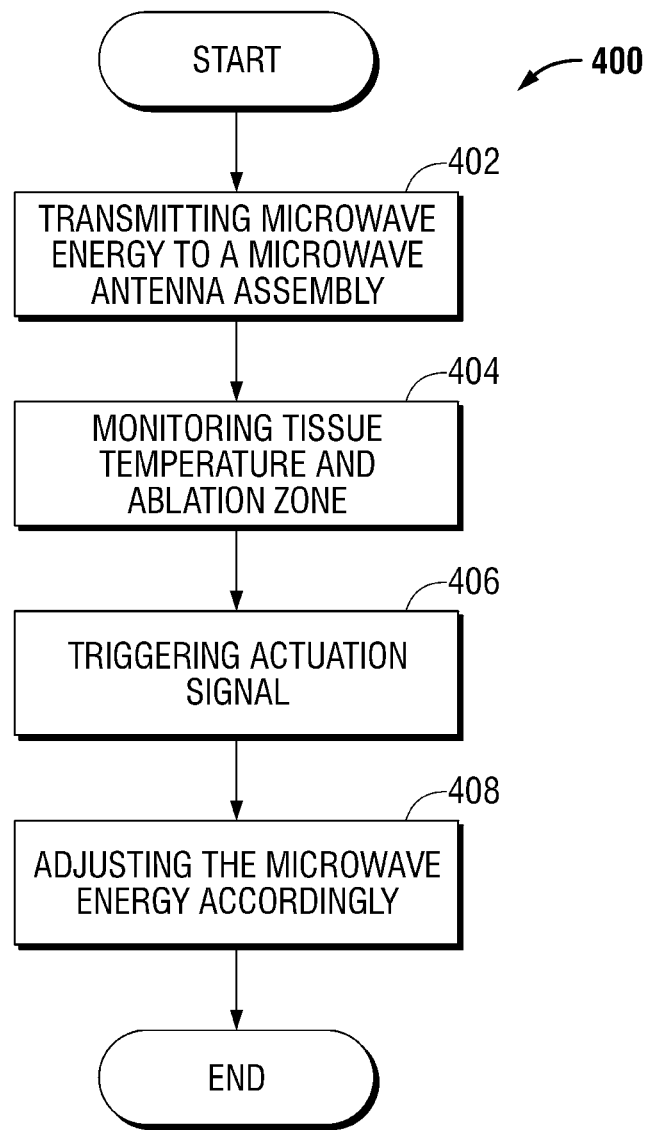
FIG. 5 is a flow chart illustrating a method for monitoring temperature of tissue undergoing ablation in accordance with the present disclosure.

With reference to FIG. 5 a method 400 for monitoring temperature of tissue undergoing ablation is illustrated. At step 402, microwave energy from generator 200 is transmitted to a microwave antenna 100 adjacent a tissue ablation site. At step, 404 reflected power $P_r$ associated with the microwave antenna is monitored. At step 406, a detection signal is communicated to the generator 200 when a predetermined reflected power $P_r$ is reached at the microwave antenna 100. At step 408, the amount of microwave energy from the generator 200 to the microwave antenna 100 may be adjusted.

From the foregoing and with reference to the various figure drawings, those skilled in the art will appreciate that certain modifications can also be made to the present disclosure without departing from the scope of the same. For example, one or more directional couplers (not shown) may be operatively associated with the generator 200, controller 300 and/or AZCM 332, and configured to direct the forward, reflected, and/or load power portions of a sampled output signal (or pulse) to the AZCM 332. More particularly, the directional coupler provides samples of the forward and reflected signal (or pulse) generated by the generator 200. The power, magnitude and phase of the generated output signal may be obtained or calculated from the measured forward and reflected signals by conventional algorithms that employ one or more suitable equations.

It should be noted that energy values or parameters (e.g., power, voltage, current, impedance, magnitude and phase) of an output pulse are valid at the output of generator 200. That is, and as alluded to above, the connector 126 and/or internal cable 126a may include transmission line losses. Accordingly, in order to get a more accurate reading and/or measurement of the energy values or parameters that are delivered to the microwave antenna 100 and/or reflected back to the generator 200, one would have to know the actual transmission line losses associated with connector 126 and/or internal cable 126a. Accordingly, in an embodiment, loss information for connector 126 and/or internal cable 126a may be determined and, subsequently, stored in memory 336 and accessed by one or more modules, such as, for example, a calibration module (600) or other suitable module (e.g., AZCM 332) for later use. The loss information for connector 126 and/or internal cable 126a may be determined by any suitable device and/or method. For example, the loss information for connector 126 and/or internal cable 126a may be determined via network analyzer 602. In one particular embodiment, the network analyzer 602 may be an integral part of generator 200 (e.g., part of calibration module 600) or, alternatively, the network analyzer 602 may be a separate handheld device that is in operative communication with generator 200. The network analyzer 602 may be used to perform a diagnostic test of connector 126 and/or internal cable 126a. The network analyzer 602 may function in a fashion similar to most conventional network analyzers that are known in the available art. That is, the network analyzer 602 may determine the properties that are associated with connector 126 and/or internal cable 126a, and more particularly, those properties that are associated with connector 126 and/or internal cable 126a that affect the reflection and/or transmission of an output signal, such as, for example, the characteristic impedance $Z_o$ of connector 126 and/or internal cable 126a.

Known line loss information associated with the connector 126 and/or internal cable 126a may be stored into memory 336 and accessed during an ablation procedure by one or more modules, e.g., AZCM 332, associated with the controller 300 and/or generator 200 and, subsequently, used in determining if a predetermined threshold value, e.g., $P_{r1-ss}$, of the reflected power $P_r$ has been met. More particularly, characteristic impedance associated with connector 126 and/or internal cable 126a may be employed to determine a more accurate or comprehensive measurement of the reflected power $P_r$. For example, a more accurate or comprehensive measurement of the reflected power $P_r$ may be determined using the equation:

$$\frac{Z_{1-ss} - Z_o}{Z_{1-ss} + Z_o} = \frac{P_{SWR} - 1}{P_{SWR} + 1} \quad (1)$$

where, $Z_o$ is the characteristic impedance associated with the connector 126 and/or internal cable 126a, $Z_{1-ss}$ is an impedance of the microwave antenna 100 when the microwave antenna 100 is positioned adjacent tissue in a "near field" at times $t_{1\text{-}ss}$, and $P_{swr}$ is a power standing wave ratio ($P_{swr}$) that may be calculated using the equation:

$$P_{SWR} = \frac{P_f + P_r}{P_f - P_r} \quad (2)$$

where $P_f$ is the power associated with the generated signal (i.e., forward signal) and $P_r$ is the power associated with the reflected signal. The characteristic impedance Zo is an accurate measure of the impedance of the connector 126 and/or internal cable 126a and takes into account the line losses associated with the connector 126 and/or internal cable 126a. In this instance, after all the necessary calculations have been carried out, an accurate representation of the reflected power $P_r$ may be transmitted to and measured by the AZCM 332 (or other suitable module associated with either the controller 300 or generator 200).

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A system for monitoring ablation size, comprising:
   a power source;
   a microwave antenna;
   an ablation zone control module configured to:
      determine a reflected power associated with the microwave antenna;
      calculate a derivative at a point taken along a control curve corresponding to the reflected power;
      determine whether the microwave antenna and tissue in a near field of the ablation zone are approaching a respective steady-state condition based on the derivative.

2. The system according to claim 1, wherein the ablation zone control module is further configured to generate a signal in response to the reflective power reaching a predetermined threshold value corresponding to a radius of an ablation zone formed by the microwave antenna.

3. The system according to claim 1, wherein the microwave antenna is configured to deliver microwave energy from the power source to tissue to form the ablation zone.

4. The system according to claim 1, wherein the ablation zone control module includes a memory.

5. The system according to claim 4, wherein the memory includes at least one data look-up table including data pertaining to the control curve varying over time and being representative of reflective power associated with the microwave antenna, the control curve including a plurality of points each of which corresponds to a value of the reflective power.

6. The system according to claim 1, wherein the microwave antenna is configured to produce a spherical ablation zone.

7. The system according to claim 1, further comprising:
   at least one fluid pump configured to supply a cooling fluid to the microwave antenna to cool one of the microwave antenna or the tissue adjacent the ablation zone.

8. The system according to claim 1, wherein the derivative is indicative of a rise and a drop in the reflected power.

9. The system according to claim 8, wherein a value associated with the measured reflected power is assigned a positive value in response to the derivative being taken during the rise of the reflected power.

10. The system according to claim 8, wherein a value associated with the measured reflected power is assigned a negative value in response to the derivative being taken during the drop of the reflected power.

11. The system according to claim 10, wherein the positive and negative values of the reflected power are indicative of the microwave antenna and the tissue in the near field of the ablation zone approaching the respective steady-state condition.

12. The system according to claim 11, wherein the positive and the negative values of the reflected power are indicative of the microwave antenna and the tissue in the near field of the ablation zone approaching an impedance match therebetween.

13. A microwave antenna adapted to connect to a power source configured for performing an ablation procedure, comprising:
   a radiating section; and
   an ablation zone control module configured to:
      determine a reflected power associated with the microwave antenna;
      calculate a derivative at a point taken alone a control curve corresponding to the reflected power; and
      determine whether the microwave antenna and tissue in a near field of the ablation zone are approaching a respective steady-state condition based on the derivative.

14. The microwave antenna of claim 13, wherein the radiating section is configured to deliver microwave energy from a power source to tissue to form an ablation zone.

15. The microwave antenna of claim 14, wherein the ablation zone control module includes at least one control algorithm stored in a memory, wherein the ablation zone control module triggers a signal when a predetermined threshold value of reflective power is measured corresponding to a radius of an ablation zone formed by the radiating section.

16. The microwave antenna of claim 13, wherein the derivative is indicative of a rise and drop of the reflected power, wherein a value associated with the measured reflected power is assigned a positive value in response to the derivative being taken during the rise of the reflected power.

17. The microwave antenna of claim 13, wherein a value associated with the measured reflected power is assigned a negative value in response to the derivative being taken during a drop of the reflected power.

18. The microwave antenna of claim 17, wherein the positive and negative values of the reflected power are indicative of the microwave antenna and the tissue in the near field of the ablation zone approaching a respective steady-state condition.

19. The microwave antenna of claim 17, wherein the positive and negative values of the reflected power are indicative of the microwave antenna and the tissue in the near field of the ablation zone approaching an impedance match therebetween.

20. The microwave antenna of claim 14, wherein the radiating portion is configured to produce a spherical ablation zone.

* * * * *